US009630182B2

(12) United States Patent
Egan et al.

(10) Patent No.: US 9,630,182 B2
(45) Date of Patent: Apr. 25, 2017

(54) NON-CONTACT INFRARED THERMOCYCLING

(71) Applicant: LEIDOS INNOVATIONS TECHNOLOGY, INC., Gaithersburg, MD (US)

(72) Inventors: Michael Edward Egan, Bothell, WA (US); Peter Karl Trost, San Diego, CA (US); James Landers, Charlottesville, VA (US); Brian Root, Charlottesville, VA (US); Orion Scott, Charlottesville, VA (US)

( * ) Notice: Subject to any disclaimer, the term of this patent is extended or adjusted under 35 U.S.C. 154(b) by 434 days.

(21) Appl. No.: 14/096,273

(22) Filed: Dec. 4, 2013

(65) Prior Publication Data

US 2015/0151302 A1  Jun. 4, 2015

(51) Int. Cl.
- *B01L 7/00* (2006.01)
- *C12Q 1/68* (2006.01)
- *B01L 3/00* (2006.01)

(52) U.S. Cl.
CPC .............. *B01L 7/52* (2013.01); *B01L 3/5027* (2013.01); *C12Q 1/686* (2013.01); *B01L 2200/147* (2013.01); *B01L 2300/0627* (2013.01); *B01L 2300/0816* (2013.01); *B01L 2300/1822* (2013.01); *B01L 2300/1844* (2013.01); *B01L 2300/1872* (2013.01); *B01L 2300/1894* (2013.01)

(58) Field of Classification Search
None
See application file for complete search history.

(56) References Cited

U.S. PATENT DOCUMENTS

| 4,632,908 | A | 12/1986 | Schultz |
| 5,232,667 | A | 8/1993 | Hieb et al. |
| 5,539,673 | A | 7/1996 | Charm et al. |
| 5,653,537 | A | 8/1997 | Ignatowicz et al. |
| 5,882,903 | A | 3/1999 | Andrevski et al. |

(Continued)

OTHER PUBLICATIONS

Niles et al. Cyclic Olefin Polymers: Innovative Materials for High Density Multiwell Plates. Assay and Drug Development Technologies 6:577-590 (2008).*

(Continued)

*Primary Examiner* — Samuel Woolwine
(74) *Attorney, Agent, or Firm* — Oblon, McClelland, Maier & Neustadt, L.L.P.

(57) ABSTRACT

A microfluidic chip includes one or more reaction chambers to hold fluids for chemical or biochemical reactions, such as PCR. A non-contact heat source heats the reaction chamber and the fluid, such that the heat source does not contact the reaction chamber or the fluid. The heat source can heat the reaction chamber and the fluid separately, where the reaction chamber and the fluid separately absorb heat radiation from the heat source. A temperature sensor acquires a temperature of the reaction chamber and/or the fluid. Control circuitry controls the heat source according to a cycling profile for the reaction in the fluid to cycle the heat source between heating and not heating the reaction chamber and the fluid based on the temperature acquired by the temperature sensor. Cooling can be provided passively or actively.

19 Claims, 12 Drawing Sheets

(56) References Cited

U.S. PATENT DOCUMENTS

| | | | |
|---|---|---|---|
| 5,928,907 A * | 7/1999 | Woudenberg | C12Q 1/6818 422/82.05 |
| 6,022,141 A | 2/2000 | Bass | |
| 6,210,882 B1 | 4/2001 | Landers et al. | |
| 6,413,766 B2 | 7/2002 | Landers et al. | |
| 6,833,536 B2 | 12/2004 | Shigeura | |
| 7,173,218 B2 | 2/2007 | Shigeura | |
| 7,294,812 B2 | 11/2007 | Shigeura | |
| 7,344,894 B2 | 3/2008 | Greenstein et al. | |
| 7,348,182 B2 | 3/2008 | Martin et al. | |
| 7,517,692 B2 | 4/2009 | Taguchi et al. | |
| 7,851,185 B2 | 12/2010 | Dale et al. | |
| 7,968,848 B2 | 6/2011 | Johnson et al. | |
| 8,007,733 B2 | 8/2011 | Shigeura | |
| 8,018,593 B2 | 9/2011 | Tan et al. | |
| 8,110,158 B2 | 2/2012 | Handique | |
| 8,124,218 B2 | 2/2012 | Unger et al. | |
| 8,133,671 B2 | 3/2012 | Williams et al. | |
| 2003/0104395 A1* | 6/2003 | McLaughlin | C12Q 1/686 435/6.16 |
| 2003/0231878 A1 | 12/2003 | Shigeura | |
| 2005/0287661 A1 | 12/2005 | Landers | |
| 2007/0009382 A1 | 1/2007 | Bedingham et al. | |
| 2010/0041056 A1 | 2/2010 | Kinnon et al. | |
| 2012/0052564 A1 | 3/2012 | Shigeura | |
| 2012/0152006 A1* | 6/2012 | Aeppli | B01L 3/502715 73/64.56 |
| 2012/0322140 A1 | 12/2012 | Shigeura | |
| 2013/0177971 A1* | 7/2013 | Chun | B01L 7/5255 435/287.2 |

OTHER PUBLICATIONS

International Search Report and Written Opinion issued Mar. 23, 2015 in PCT/US2014/057992.

Bienvenue et al., An integrated microfluidic device for DNA purification and PCR amplification of STR fragments, Forensic Science International: Genetics 4, 2010, pp. 178-186.

Hagan et al, "An integrated, valveless system for microfluidic purification and reverse transcription-PCR amplification of RNA for detection of infectious agents," Lab Chip, 2011, 11, pp. 957-961.

Ichikawa et al., "Extension of a DNA Molecule by Local Heating with a Laser," Physical Review Letters, PRL 99, 148104, Oct. 2007.

Jena et al., "Micro fabrication of cyclic olefin copolymer (COC) based microfluidic devices," Microsyst Technol (2012), 18: 159-166.

Shin et al., "Chemical Structure and Physical Properties of Cyclic Olefin Copolymers," Pure Appl. Chem., vol. 77, No. 5, pp. 801-814, 2005.

Office Action issued Jul. 12, 2016 in European Patent Application No. 14786400.3.

* cited by examiner

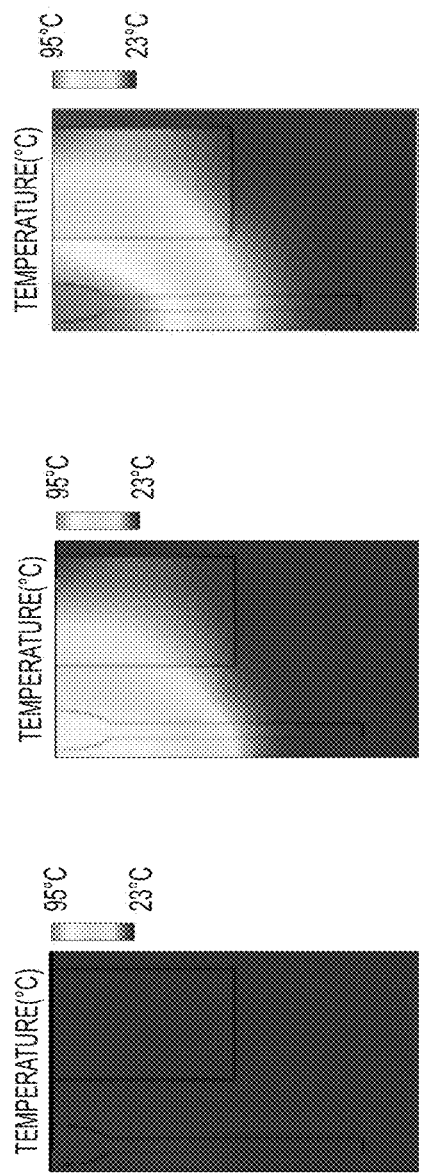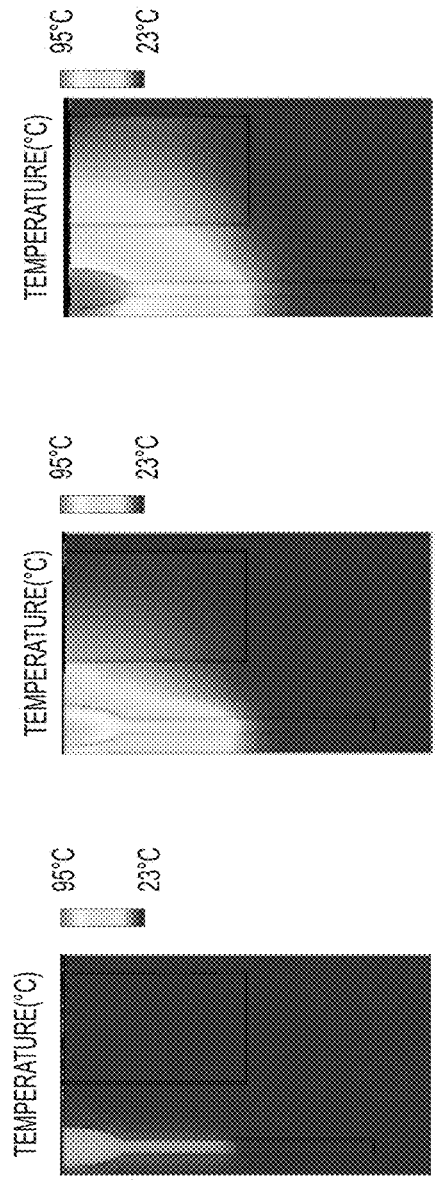
FIG. 8A  FIG. 8B  FIG. 8C  FIG. 8D  FIG. 8E  FIG. 8F

NON-CONTACT INFRARED THERMOCYCLING

BACKGROUND

Polymerase Chain Reaction (PCR) is a process utilized in biochemical laboratories, to replicate oligonucleotides using polymerase enzymes, such as Taq polymerase. PCR enables rapid replication of oligonucleotides, in particular DNA, so that single copies of an oligonucleotide can be transformed into a significant concentration to enable further manipulation or analysis. The PCR process involves: cycling the temperature of the reaction mixture between two or three temperatures repeatedly to enable replication of the target oligonucleotides. Each cycle can double the number of target oligomer sequences. PCR techniques can amplify a single molecule of an oligonucleotide or oligoribonucleotide about $10^6$ to about $10^9$-fold. A separate assay step can include detecting the amplified oligonucleotides. See U.S. Pat. No. 7,955,840, which is incorporated herein by reference.

The MATCI device disclosed in U.S. Pat. No. 5,589,136 (Northrup, Raymond P. Mariella et al. 1996) is an automated PCR device that uses a modular approach to thermal cycling and analysis. In this patent, which is incorporated herein by reference, each reaction is performed in its own thermal cycling sleeve, and each sleeve has its own associated optical excitation source and fluorescence detector. The low thermal mass of the thermal cycling sleeve allows the MATCI device to realize extremely fast thermal cycling: samples can be heated at a rate of up to 30° C./sec. and cooled at rate as great as 5° C./sec.

Two other commercially available systems, sold under the trade names GENEXPERT (Cepheid, Sunnyvale, Calif.) and RAZOR (Idaho Technology, Inc.), use disposable fluidic cartridges, each containing a flexible reaction chamber that expands under pressure to make tight contact with a solid heater located in the instrument (Petersen, McMillan et al. 1999). RAZOR uses a flexible fluidic pouch and actuators that move a reaction slug within the pouch. The reaction zone walls of the pouch make tight contact with two solid heaters. In both cases, the heater is a solid and the disposable cartridge or pouch contains one or more reaction zones, each with a thin, flexible wall that makes thermal contact with the heater. Another technology, sold commercially under the trade names TRUDIAGNOSIS™ and TRUARRAY™ by Akonni Biosystems (Fredericksburg, Md.), rapidly screens a sample for hundreds of disease markers at one time by using hundreds of molecular biosensors arrayed in a microarray the size of a fingernail. The samples are conveyed through the array using microfluidic channels. The Akonni Biosystems technology can provide accurate diagnostic results in less than 30 minutes to support an informed and timely treatment decision.

SUMMARY

An apparatus according to an exemplary aspect of this disclosure can include a reaction chamber to hold a fluid; a non-contact heat source to heat the reaction chamber and the fluid, wherein the heat source does not contact the reaction chamber or the fluid, and the reaction chamber and the fluid separately absorb heat radiation from the heat source; a temperature sensor to acquire a temperature of the reaction chamber and/or the fluid; and a control circuit to control the heat source according to a cycling profile for a chemical or biochemical reaction in the fluid to cycle the heat source between heating and not heating the reaction chamber and the fluid based on the temperature acquired by the temperature sensor.

The material of the reaction chamber can be significantly heated by the heat source separately from the heating of the fluid by the heat source.

A microfluidic chip can be included that includes the reaction chamber together with a plurality of other reaction chambers.

The heat source can include an output for non-contact heating for each of the reaction chambers, where the temperature sensor is to acquire a separate temperature for each of the reaction chambers, and the control circuit is to control the heat source independently for each of the reaction chambers based on the respective temperatures acquired by the temperature sensor and the cycling profile.

The heat source includes one or more infrared lasers.

The microfluidic chip can include COC (cyclic olefin copolymer).

The one or more infrared lasers can operate at 1720 nm+/−10 nm center wavelength.

The temperature sensor can be a non-contact sensor that does not contact the reaction chamber or the fluid.

The temperature sensor can include one or more pyrometers or one or more infrared cameras.

The cycling profile can include the following steps: (a) heating to a first temperature at a first rate; (b) holding the first temperature for a first holding time; (c) cooling to a second temperature at a second rate; (d) holding the second temperature for a second holding time; (e) heating to a third temperature at a third rate; and (f) holding the third temperature for a third holding time.

In the cycling profile, the steps (a)-(f) can be repeated for a predetermined number of cycles.

For a last one of the cycles, the third temperature can held for a final extension time period that is longer than the third time period.

The cycling profile can include, prior to the step (a) in a first one of the cycles, a denaturing step of holding a denaturing temperature for a denaturing time period.

The control circuit can be to control the heat source according to the cycling profile such that the following conditions are satisfied: volume of the fluid ≤10 ml; the predetermined number of cycles=20-35; the first temperature=50-96° C.; the first holding time=2-10 seconds; the first rate=>3° C./s; the second temperature=50-96° C.; the second holding time=5-20 seconds; the second rate: <−2° C./s; the third temperature=50-96° C.; the third holding time=5-20 seconds; the third rate=>3° C./s; and the final extension time period=2-15 minutes.

The control circuit can be to control the heat source according to the cycling profile such that the following conditions are satisfied: denaturing temperature=50-96°; and denaturing time period is equal to or more than 60 seconds.

The control circuit can be to control the heat source according to the cycling profile such that the following conditions are satisfied: volume of the fluid ≤10 ml; the predetermined number of cycles=27; the first temperature=95° C.; the first holding time=5 seconds; the first rate=>3° C./s; the second temperature=60° C.; the second holding time=10 seconds; the second rate=−2.1° C./s; the third temperature=72° C.; the third holding time=10 seconds; and the third rate=3.7° C./s. These values can be approximate values or averaged values in some implementations.

The control circuit can also be to control the heat source according to the cycling profile such that the following conditions are satisfied: volume of the fluid ≤10 ml; the predetermined number of cycles=27; the first temperature=94° C.; the first holding time=10 seconds; the first rate=>3° C./s; the second temperature=59° C.; the second holding time=40 seconds; and the second rate=−2° C./s. These values can be approximate values or averaged values in some implementations.

In one implementation, the control circuit can be to control the heat source according to the cycling profile such that the following conditions are satisfied: the first temperature is higher than the second and third temperatures; the third temperature is higher than the second temperature; and the first holding time is less than the second holding time and less than or equal to the third holding time.

An active cooler can be provided to cool the reaction chamber and/or the fluid, wherein the control circuit can be to control the active cooler to provide cooling in accordance with the cycling profile.

The heat source can include an IR (infrared) light source and a fiber optic channel to output IR light from the IR light source to the reaction chamber and the fluid to heat the reaction chamber and the fluid, and the fiber optical channels can include corrective lenses at output ends thereof.

A method for a reaction (e.g., a PCR reaction) can include: controlling, by a control circuit, heating and cooling of a reaction chamber that contains a fluid in which the reaction is to occur, in accordance with a cycling profile based on sensing a temperature of the reaction chamber or the fluid, the cycling profile including: (a) heating to a first temperature at a first rate; (b) holding the first temperature for a first holding time; (c) cooling to a second temperature at a second rate; (d) holding the second temperature for a second holding time; (e) heating to a third temperature at a third rate; and (f) holding the third temperature for a third holding time.

A non-transitory computer-readable medium can include computer-executable instructions, which when executed by a control circuit, cause the control circuit to perform the method.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 7b illustrates a heat map of the IR laser source of FIG. 7a;

FIGS. 8a-f illustrates heat simulations using two different wavelengths directed to a cartridge/chamber combination;

DETAILED DESCRIPTION

Figure 1:
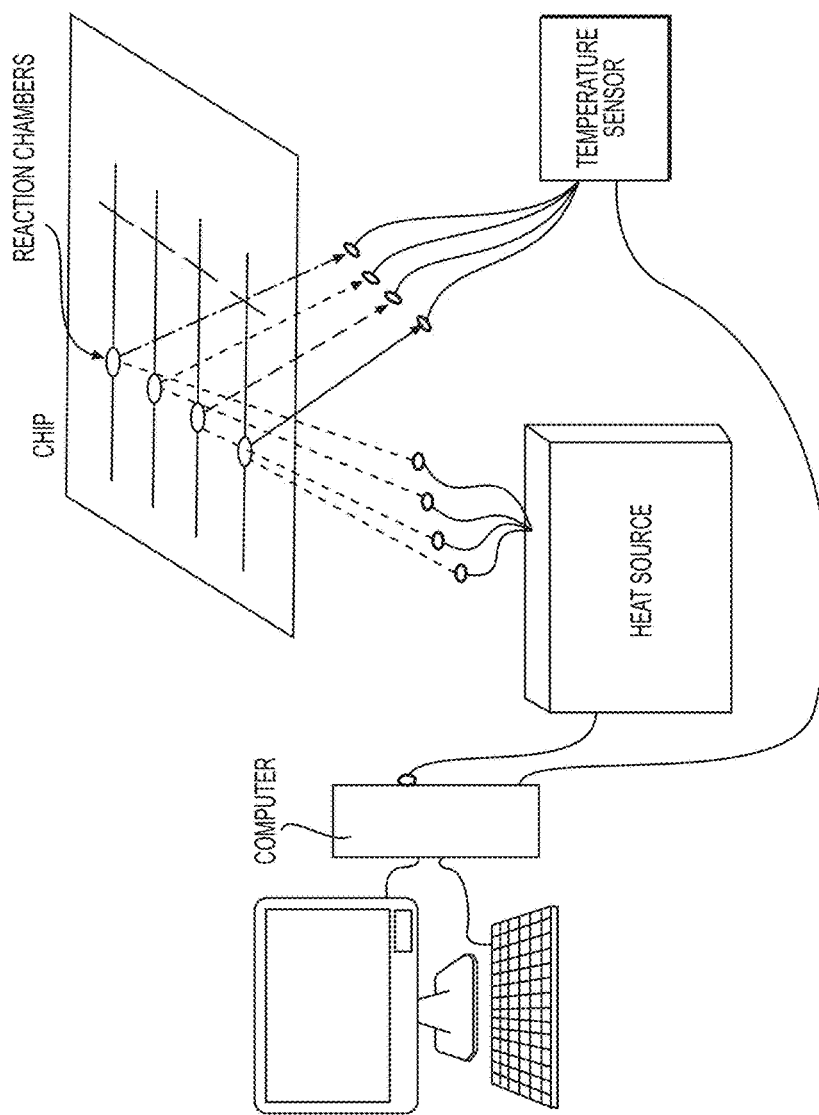
FIG. 1 is a schematic illustration of a system including a computer, a heat source, a temperature sensor, and a chip.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise.

Furthermore, the terms "about," "approximately," "around," and similar terms generally refer to ranges that include the identified value within a margin of 20%, 10%, or preferably 5%. The terms also refer to ranges that include the identified value within a margin of: 2, 1, or 0.5° C.; 1, 2, or 5 seconds; or 1 or 0.5° C./second.

Overview of Exemplary Implementations

Genetic information can be used to establish the identities of individuals and the types of organisms, and PCR is capable of creating analyzable quantities of genetic material from very small samples. Many technologies exist to facilitate the application (sometimes referred to as amplification) of PCR to analytical and forensic tasks. In particular, the use of PCR to identify unidentified bodies and criminals is widely used in law enforcement and the military. The application of PCR to national defense and homeland security is also an area of active biodefense development. Also, doctors and hospitals can use PCR technology in the following procedures: screening blood, saliva, or urine samples for multiple infectious diseases associated with upper respiratory, intestinal, or STD infections; determining whether an infectious disease is resistant to antibiotics; determining whether an infection is viral or bacterial; identifying an individual's susceptibility to an adverse drug reaction; diagnosing a cancer type (e.g., breast, prostate, ovarian, or pancreatic); and identifying an individual's predisposition to Alzheimer's disease. This list is not comprehensive. An automated and portable PCR apparatus/device can process small sample concentrations on-site at remote locations to provide analytical data to investigators and medical workers.

A fundamental operation during the PCR process is thermal cycling, i.e., the raising and lowering of reaction temperatures to enable the amplification process, in which the temperature of the reaction mixture is driven between about 60° C. and about 95° C. as often as twenty times or more. In another implementation, the reaction mixture is driven between about 60° C. and about 95° C. as often as fifty times or more. A thermal cycle can have four segments: heating the sample to a first temperature; maintaining the sample at the first temperature; cooling the sample to a lower temperature; and maintaining the temperature at the lower temperature.

A conventional PCR instrumentation can use an aluminum block holding as many as ninety-six conical reaction tubes in which the sample and necessary reagents for amplication are contained. The block is heated and cooled during the PCR amplication process, often using either a Peltier heating/cooling apparatus, or a closed-loop liquid heating/cooling system in which flowing through channels machined into the aluminum block. However, the large mass of the aluminum block, and the conductivity of aluminum, can limit the rates of heating and cooling to about 1° C. per second. Consequently, a fifty-cycle PCR amplification process takes at least about two hours. See, e.g., U.S. Pat. No. 7,955,840.

Moreover, the cooling rate of the aluminum block is significantly lower than the heating rate. The asymmetry between the heating and cooling rates reduces the efficiency of the PCR process. For example, unwanted side reactions can occur at temperatures between the extremes creating unwanted DNA products, such as so-called "primer-dimers" and anomalous amplicons that consume reagents necessary for the desired PCR reaction. Other processes, e.g., ligand binding (organic or enzymatic) also suffer from unwanted side reactions under non-uniform temperatures that often degrade the analysis. For these reasons, optimization of the PCR process and similar biochemical reaction processes requires that the desired optimal reaction temperatures be reached as quickly as possible, spending minimal time at intermediate temperatures. Therefore the reaction vessels containing the reactants must be designed to optimize heating and cooling rates, to permit real time optical interrogation, and to accept various sample volumes. See, e.g., U.S. Pat. No. 7,955,840.

Further, conventional approaches to handling thermal cycling are limited, depending on flexibility in the disposable component to create satisfactory thermal contact with the instrument hardware. In particular, methods and apparatus that provide the desired cycling performance without reliance on special reaction chamber materials offer the promise of reduced cost and greater efficiency.

PCR reactions, as used in research, biomedicine, human identification and more, can require several hours to complete. In accordance with this disclosure, efficient methods for temperature cycling the reaction mixture can speed up the reactions and reduce the reaction time needed to 45 minutes or less. Such an efficient method can be referred to as rapid thermo-cycling, which can be provided by non-contact infrared (IR) heating, in accordance with at least some of the exemplary implementations described herein.

IR heating can be provided by an IR laser, and can offer exceptional levels of accuracy and control in cycling parameters. However, it is preferred that a distribution of heat in the reaction chamber is uniform and tightly controlled so that heat-driven reactions are driven completely with every thermal cycle.

Exemplary implementations according to this disclosure can offer, amongst other things, a novel way to ensure that the heat from a non-contact source, like an IR laser, is sufficiently distributed around the reaction chamber, so that optimum reaction conditions are achieved. Without a strategy to uniformly heat the reactants and solution, temperature gradients may develop in the reaction chamber, which can result in incomplete or inefficient reactions, and which would require slower thermal cycles.

According to exemplary implementations, the wavelength of an electromagnetic source is chosen and optimized to be absorbed by both a reaction chamber and the contents of that chamber. With heat absorption from the reaction chamber material and the reactants/solvents inside the chamber, temperatures can be uniformly distributed among the reactants so that they react uniformly. A specific example of a reaction chamber is in a micro fluidic chip, made from a cyclic olefin copolymer (COC), such as ZEONOR, which is a registered trademark of ZEON CHEMICALS L.P., where the chip includes a micro-liter level volume of Polymerase Chain Reaction (PCR) reactants in a buffer solution. A non-contacting IR laser is used to heat the reaction chamber to a specified temperature or specified temperatures necessary for the PCR reaction to proceed. A pyrometer, also not in contact with the substrate, can be used to monitor the temperature of the reaction chamber and transmit temperature readings to a computer, which is used to regulate and control power to the IR laser.

Exemplary implementations according to this disclosure can provide the following advantages: (1) replacing contacting means for heating offers greater control over the temperature cycling, and (2) in small volumes, where a surface-to-volume ratio is high, heat will escape from the solution into the adjacent chamber material at a rapid rate even with more efficient heating of the solution itself; heating the solution and the chamber simultaneously is more efficient at avoiding temperature gradients.

Introduction

Methods, processes, procedures, systems, devices and components for performing accurate and rapid thermocycling in a micro-total analysis system, such as microelectromechanical systems (MEMS) and microfluidics, are described herein. Precise apparatus architecture and features within a cartridge and instrument system to rapidly heat and cool a reaction chamber with a radiation source that is not in contact with a substrate (or other reaction site) are also described herein. The exemplary implementations described herein can be tuned for rapid and efficient temperature control in a user-manipulated device where spatial accuracy to a micrometer level is required.

Aspects of this disclosure relate to non-contact heating of a reaction chamber for biological analysis. Aspects of this disclosure also relate to microfluidics for the analysis of nucleic acids. Aspects of this disclosure further relate to non-contact thermal cycling in a microfluidic chip.

Aspects of this disclosure can provide a rapid heat transfer for chemical and biochemical reactions at the mesoscale and microscale. Conventional, reaction chambers can be heated by both contacting and non-contacting means. Non-contacting means allows potentially more rapid, accurate, and controlled methods for thermal cycling.

Microfluidic chips are widely applied to forensics, diagnostics, environmental monitoring and a variety of other fields. The chips generally use PCR reactions to amplify target DNA for identification. The DNA may be from human, animal, bacteria, fungus, virus, or any organism that contains DNA. These chips and instruments that connect to the chips are meant to use small amounts of a sample, and therefore small amounts of DNA for detection, and rapidly amplify the DNA using PCR techniques, so that target sequences on the DNA can be analyzed.

PCR methods generally require temperature changes in a cyclic method to amplify the target DNA. The temperature changes facilitate melting, annealing, and extending the DNA sequences in a cycle that drives rapid amplification.

Many different chemical, biochemical, and other reactions are sensitive to temperature variations. Examples of thermal processes in the area of genetic amplification include, but are not limited to, Polymerase Chain Reaction (PCR), Sanger sequencing, etc. One approach to reducing the time and cost of thermally processing multiple samples is to use a device including multiple chambers in which different portions of one sample or different samples can be processed simultaneously. Examples of some reactions that may require accurate chamber-to-chamber temperature control, comparable temperature transition rates, and/or rapid transitions between temperatures include, e.g., the manipulation of nucleic acid samples to assist in the deciphering of the genetic code. Nucleic acid manipulation techniques include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

Physical methods to achieve thermal cycling have been developed to make the PCR cycling time as short as possible. There are a variety of methods for thermal cycling, both including and excluding a microfluidic chip. There are contact methods, such as peltier heating, where two bodies are put in physical contact to change the temperature for cycling. Another method, in accordance with this disclosure, is non-contact heating, wherein an optical or other source of radiation is directed to the body containing reagents and samples to be cycled at a distance. This non-contact method can provide advantages over contact methods for a variety of reasons including more rapid thermal cycling and sharper heating gradients.

Cooling of reaction chambers can be active or passive. An active cooling mechanism can include a fan or other non-contact method. A contact cooling method, such as a peltier or heat sink, can also be utilized. An advantage that is achievable with the non-contact heating method is that active cooling is not necessary, but still could be utilized. The substrate may be in thermal communication with other materials and passively draw away heat when the heating source is off.

An issue to address with non-contact heating from a light source is the provision of appropriate heat transfer in the region of the sample. A substrate holding a liquid sample can be detrimental to attempts to achieve specific uniform temperatures in the liquid sample. The material of the chamber may disperse the heat from the liquid sample if the heat source is tuned only to wavelengths that the liquid or components of the liquid are heated efficiently.

Thermal regulation of reactants or assay elements can be achieved through bulk heating of the cartridge using heaters such as electrical resistance heaters, Peltier heating and cooling cells, air heaters, or infrared heaters. Such bulk-heating systems are usually large, and have generous energy supplies. Currently, most microfluidic devices fit on a benchtop. In accordance with aspects of this disclosure, space efficient devices or miniaturized devices can be provided, enabling handheld, portable size dives. Such devices can require relatively smaller volumes than bench-top systems. Volumes for such systems range between $10^{-1}$ and $10^3$ microliters. A portable device can heat volumes of 1-5 microliters of assay elements, such as a blood sample, and/or 100-500 microliters of assay elements, such as reagents. Restricting the volume to be heated to the temperature-controlled zones reduces the amount of heat required and facilitates localized heating.

Sensors can be used in mesoscale and microscale analysis devices. When energy is radiated from an object, the radiated energy can be used according to various implementations to make a determination of the temperature of the object. The energy can be in the visible light spectrum or in the non-visible light spectrum. As the energy strikes a detector in a sensor, a reaction occurs that can result in an electrical signal output from the detector. The electrical output can be a signal that can be processed, for example, amplified and/or linearized, as desired, to calculate temperature according to conventional pyrometer or other temperature sensing techniques.

Circuits, signal processing systems, temperature sensors, heaters, and related devices that are relevant to this disclosure are described in U.S. Pat. No. 4,632,908 (Schultz, 1986); U.S. Pat. No. 5,232,667 (Hieb and Blomberg, 1993); U.S. Pat. No. 5,653,537 (Ignatowicz et al., 1997); U.S. Pat. No. 5,882,903 (Andrevski et al., 1999); U.S. Pat. No. 5,539,673 (Charm et al., 1996); and U.S. Pat. No. 6,022,141 (Bass, 2000), which are incorporated herein in their entireties by reference.

Methods of using electromagnetic radiation to heat only a liquid in a chemical/biochemical reaction chamber that are relevant to this disclosure are described in U.S. Pat. Nos. 6,210,882 and 6,413,766 (Landers et al., 2001, 2002), which are incorporated herein in their entirety. These patents describe non-contact heating methods that lack uniform heating and lead to temperature gradients in the sample and an incomplete reaction.

Further methods that are relevant to this disclosure are described in U.S. Pat. Nos. 6,833,536, 7,173,218, 7,294,812, and 8,007,733 (Shigeura, 2004; Shigeura, legal representative and Shigeura, deceased, 2007a, 2007b; Shigeura and Shigeura, 2011), which are incorporated herein in their entirety. These patents describe a non-contact heating method with a non-contact temperature sensing that also leads to non-uniform heating by avoiding interaction with the substrate.

In U.S. Pat. No. 7,344,894 (Greenstein et al., 2008), incorporated herein in its entirety, a device is described to heat with a non-contact method, that also fails to make a uniform, or sufficient heating area for a sample.

In U.S. Pat. No. 7,348,182 (Martin and Saul, 2008), incorporated herein in its entirety, a method is described that is susceptible to hotspots, requires a waveguide, and results in non-uniform heating.

In U.S. Pat. No. 7,517,692 (Taguchi and Kitamura, 2009), a reaction chamber is heated by non-contact means, but does not accomplish any sort of accuracy or detail, and fails to accomplish uniform, controlled heating.

Detailed Discussion of the Exemplary Implementations

According to the exemplary implementations discussed herein, proper tuning of light-mediated non-contact heating for a chamber holding a sample and the sample can be achieved. In a microfluidic reaction chamber, the sample is a very small (microliter to nanoliter) volume, that is in thermal contact with the surfaces of the chamber. Such a small sample develops thermal gradients near the chamber-sample interface because of the high surface to volume ratios and the fact that the substrate material, composing the chamber, is a greater thermal sink than the liquid sample. The chamber may be a variety of materials, including but not limited to glass, plastic, silicon, ceramic, quartz or other polymeric substrate (such as polymethylmethacrylate, polycarbonate, polyethylene, cyclic olefin, or polydimethylsiloxane). Preferably the substrate is poly (cyclic olefin) or cyclic olefin copolymer. The material may make up any sort of chamber containing a sample, but this is especially applicable to a microfluidic chip. Various fluid-processing components are linked by microchannels on the microfluidic chip. The ranges of channel dimensions can include the microchannels are about 10 mm to about 80 mm in length and the microchannels are about 10 um to about 200 um across.

Heating the liquid directly in a chamber of any material limits the uniform temperature of the full liquid sample, because the interfaces between the liquid sample and the material have different thermal properties than the sample portion that is not in contact or furthest from the material. There is a thermal gradient that makes the reactions in the sample inefficient.

A solution is to drive temperature changes and heat flow in both the liquid and the chamber material at the same time. In small samples and small chambers, like those found on a microfluidic chip, the surface area and volume of the chamber material and surrounding material is sufficient to bring the liquid sample to a target temperature through thermal contact. In high surface-area to volume chambers, it is most efficient to heat the chamber material efficiently with the heating source. The heated chamber material will efficiently and uniformly heat the sample volume.

The radiation heat source can be one of a variety of different source, including, but not limited to infrared (IR) laser, IR diode, LED, VCSELs, or microwave sources.

Various implementations include a system that includes a non-contact radiant heater and a non-contact temperature sensor for a chemical or biochemical reaction chamber. The heater can be designed to emit radiation having a wavelength of, for example, about 0.7 micrometers or longer, or about 1.5 micrometers or longer. The heater can be, for example, a laser source or a halogen light source. The sensor can detect radiant energy emitted from the reaction chamber without contacting the reaction chamber. According to various implementations, the sensor can detect radiant energy having a wavelength of from about two micrometers to about 20 micrometers, for example, a wavelength of from about 5 micrometers to about 15 micrometers. The sensor can be, for example, one or more non-contact infrared pyrometers. The sensor can also be one or more infrared cameras.

According to various implementations, a non-contact heating and temperature sensing system is provided for regulating temperature within a chemical reaction chamber. The reaction chamber can be formed in a substrate or can be fixed, secured, mounted, or otherwise attached or connected to a surface of a substrate or to a holder.

According to various implementations, a non-contact radiant energy source is used to heat a reaction region to effect or promote a chemical and/or biochemical reaction. The reaction region can be within an analytical instrument such as a polymerase chain reaction (PCR) device, a medical diagnostic device, a DNA purification instrument, a protein or blood gas analyzer, or other instrument. The energy source can be designed to emit energy having a wavelength sufficient to carry out a desired reaction or desired reaction rate. For example, the energy source can emit energy having a wavelength of at least about 0.7 micrometers, but this is not limiting.

Many DNA amplification methods can be used for this device including the PCR or isothermal methods. Extension of DNA through heating of a substrate by a laser is a useful application.

Aspects of this disclosure are exemplified in a process in which extraction and amplification processes are combined into a single, closed-chamber reaction. This approach is preferred because it simplifies the design and operation of automated devices and maintains integrity of the sample. However, according to other exemplary implementations, this approach is not essential. For this example, the combined extraction-PCR method described in US 2010/041056 (Kinnon and Saul, 2010), which is incorporated herein by reference, can be utilized. An ability to use a single chamber for all reactions substantially reduces a need for fluidic movement and thereby, simplifies the design of the device and reduces failure rate and operation time.

The system containing the chip, heat source, and sensing source may be computer controlled, so that the temperature is accurately controlled within a degree.

The chip may have multiple channels, which are all being heated at the same rates with the same power, or with different rates, power or temperature levels.

The reaction chamber may be active cooled, such as with compressed air or a fan, or passively cooled by natural radiative dissipation from the chamber.

The chip or cartridge may be static, or held in place, for the instrument to adjust to the sample, or it may be a circular design such that the chambers and sample are moved or rotated to be in the radiation or cooling path. The chip or cartridge may have 1 to 20 channels. In some embodiments it may have more than 20 channels.

With reference now to the drawings, FIG. 1 schematically illustrates a system including a heat source, a chip, and a sensor for a four channel chip with feedback control by a computer. The four channel chip is merely exemplary and other numbers channels or a single channel can be utilized.

In FIG. 1, a computer is connected with data cables to a first heat source, such as a laser source, and a temperature sensor, such as a pyrometer. In this particular exemplary implementation, since the chip has four channels (and four reaction chambers), the first source has four heat outputs that are independently controlled by the computer, either automatically through an algorithmic routine or based on user input, to heat the four reaction chambers at a one-to-one correspondence. Further, since the chip has four channels, the temperature sensor has detectors that collect temperatures, separately, of each of the reaction chambers.

In a further implementation, a second heat source is provided and connected to the computer. The second heat source can have four outputs (in a one-to-one correspondence as in the case with the first heat source) to each the four reaction chambers. The second heat source can heat the reaction chambers at a different wavelength than the first heat source. Further, additional heat sources can be provided, with respective outputs operating at different wavelengths.

Each of the heat sources can be coupled to the computer and independently controlled on a per reaction chamber basis. In an exemplary implementation, each of the heat sources is a laser source that outputs light at a different wavelength. Additionally, multiple temperature sensors can be provided to monitor different portions of the reaction chamber and/or the chip.

A wavelength of light used to heat the sample can be tuned to one or more optimum wavelengths for heating the chamber material and the liquid sample simultaneously. In particular, one wavelength can be used to heat both the chamber material and the liquid sample simultaneously, or two or more wavelengths can be used to heat the chamber material and the liquid sample simultaneous. When the two or more wavelengths are used, each of such wavelengths can be an optimum wavelength for only one of the chamber material and the liquid sample, or each of such wavelengths can be selected such that resultant heating provided by the wavelengths, when used together, provides a uniform temperature increase between the chamber material and liquid sample. In such an implementation, a first wavelength of the wavelengths can heat one of the chamber material and the liquid sample, while a second wavelength of the wavelengths can heat the other of the chamber material and the liquid sample. Further, the first wavelength can heat the one of the chamber material and the liquid sample to a greater degree than the other of the chamber material and the liquid sample, where the second wavelength can heat the other of the chamber material and the liquid sample to a great degree than the one of the chamber material and the liquid sample. The wavelengths can be output at different power levels based on absorbency characteristics and volume of the material/liquid being heated.

Two or more wavelengths can be generated by, e.g., two or more separate laser sources. Outputs of the two or more separate laser sources can be coupled together by fiber optic couplers to a single fiber optic cable, which provides an output path to a target/sample/reaction chamber.

The chamber can be provided on a microfluidic chip and the heating source can be an infrared source, such as an infrared laser. The material of the substrate can be COC (cyclic olefin copolymer), or COP (Cyclic Olefin Polymer). This material can be the material for the reaction chamber or for the entire chip. The liquid sample can be a sample including DNA and PCR reagents to perform DNA amplification in the chamber. Heating of the chamber and the liquid sample can be efficient enough to drive rapid PCR in the chamber from rates as low as 3° C./s to 100° C./s. A complete thermocycle can be completed in about 20 seconds. However, lower rates can be achieved if desired for a particular implementation by, e.g., limiting an output power.

Figure 2:
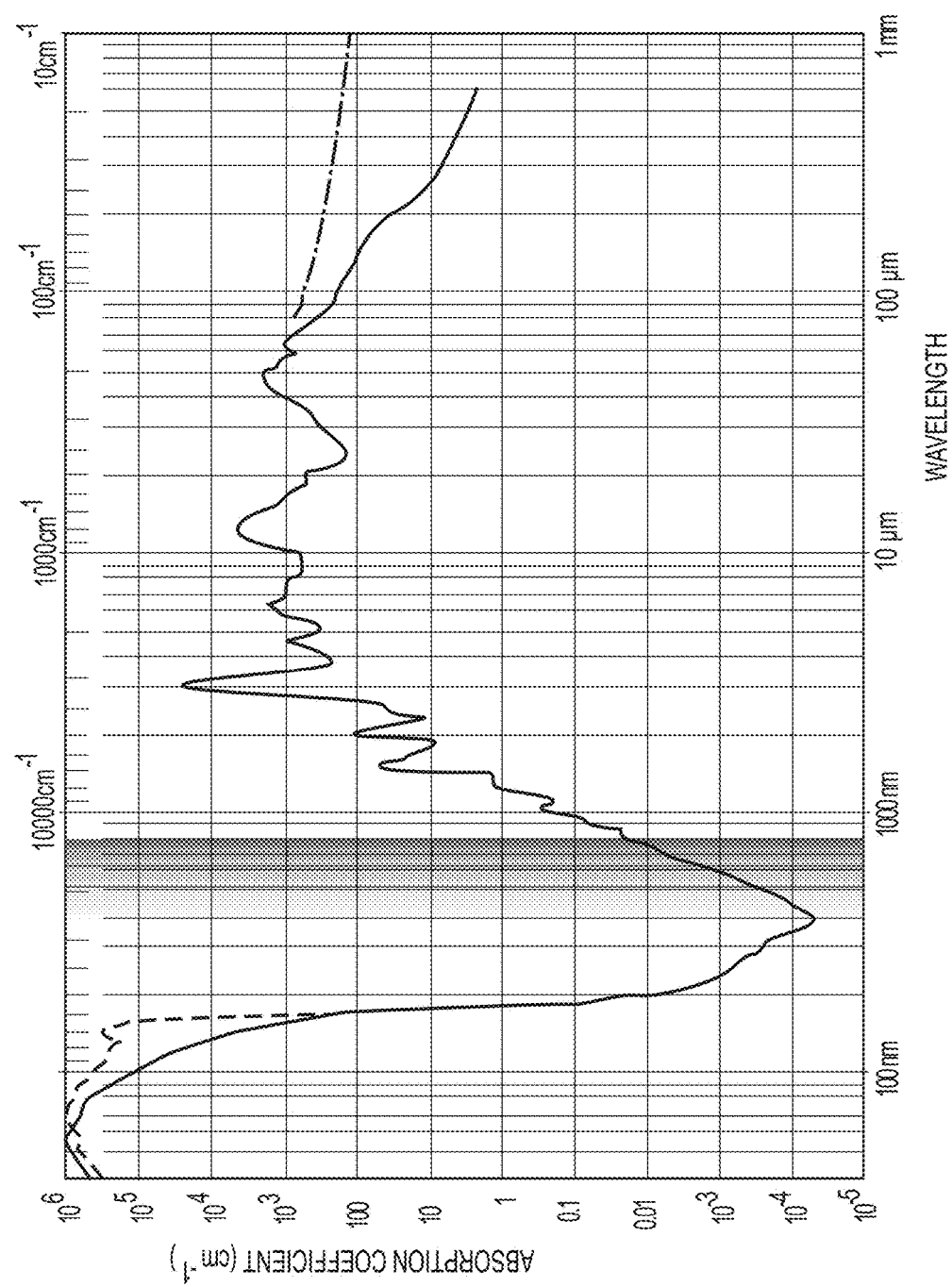
FIG. 2 illustrates an infrared (IR) absorption spectrum for water.
Figure 3:
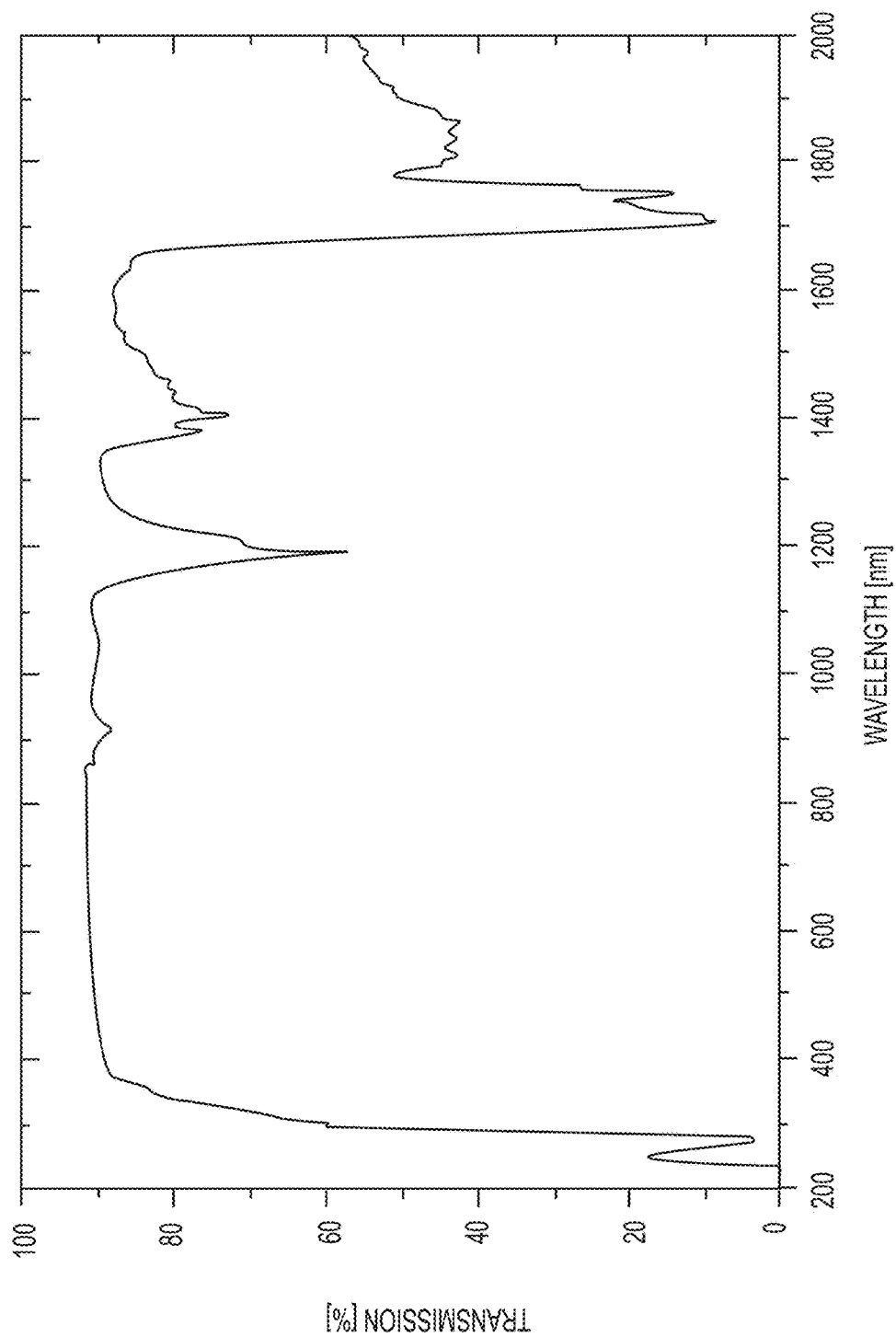
FIG. 3 illustrates an IR absorption spectrum for cyclic olefin copolymer (COC)

The heat source can be referred to as a radiation source, and can be a laser tuned to a wavelength of 1720 nm, which is readily absorbed by COC substrate material and water, which can comprise a main portion of the liquid sample. The ratio of absorbed radiation depends on a thickness of each material/substance in total cross section. FIG. 3 illustrates spectral data on the absorption of light in COC and FIG. 2 does the same for water. The thickness of the COC is 2 mm for the data shown. At 1720 nm, there is about a 20% transmission of light, which is about 0.23/mm absorption. Water shows about 5.7/cm absorption, or 0.57/mm. With these dimensions, water absorbs about twice the light energy as compared to the COC substrate, but there is substantially more COC present, given the volume of the reaction chamber (approximately 1.35 microliters) compared to the volume of the COC material heated.

The substrate material is selected so as to significantly absorb light or heat, so that the substrate (i.e., the reaction chamber) itself is heated by the heat source, separately from heating of the fluid by the heat source. By "significant," what is meant is that the substrate material is heated in a similar manner as the fluid within the reaction chamber, and does not merely transmit light or heat to the fluid without itself being heated in a manner similar to the fluid.

Cooling in this example is passive in that the radiation source is turned off when the temperature is meant to be lowered. An alternative embodiment includes small fans for each chamber to for active cooling. Such fans or the turning off of the radiation source is controllable by the computer, which receives temperature data from the temperature sensor, and can compare a detected temperate to that of a threshold value, and can maintain a set temperature or temperature range based on the detected temperature.

The reaction chamber can be provided on an integrated chip, which can include extraction, amplification, and separation modules (regions, physical structure). The reaction chamber described is for DNA amplification, including primers, reagents and the extracted DNA.

According to an exemplary implementation, the IR laser source is 21 mm or more away from the reaction chamber and is separated into 4 optical channels, one for each channel on the 4 microfluidic channel chip. Exemplary distances between the IR laser source and the reaction chamber are 25.40 mm (1.000 inches), 32.33 mm (1.273 inches), and 34.87 mm (1.373 inches). A corresponding laser spot covering the reaction chamber and substrate is approximately 6.7 mm in diameter. However, other laser spots can be achieved.

The IR laser source can be arranged such that the 4 (or more) optical channels are substantially normal to the substrate at a position of a respective reaction chamber. The channels can also be at a relatively small angle of inclination. A non-contact temperature sensor can be provided at an angle with respect to the normal. The angle can be between 30-60° or 45°. A separate non-contact temperature sensor channel can be provided for each respective reaction chamber. The non-contact temperature sensor (or channel thereof) can be provided 15 mm (0.590 inches) away from a respective reaction chamber.

Figure 4A:
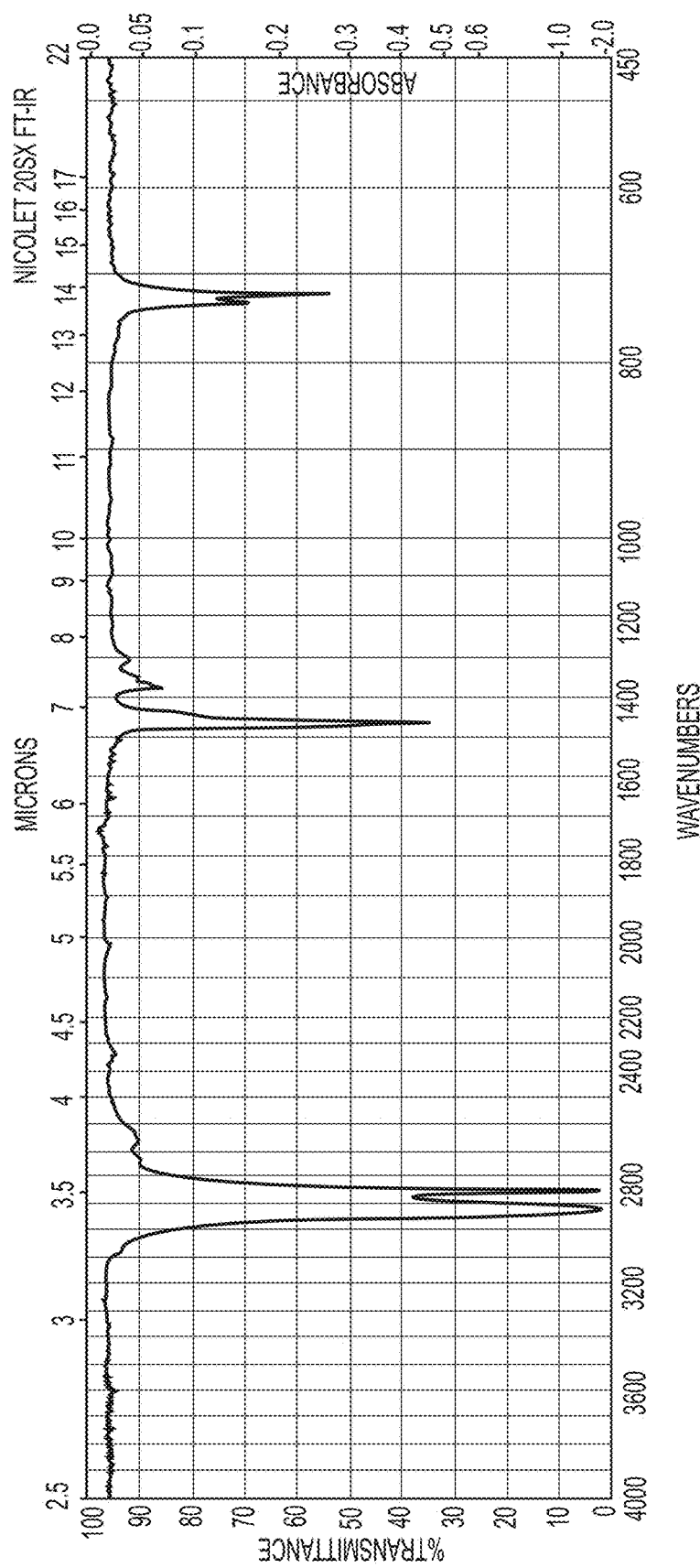
FIG. 4a illustrates an IR absorption spectrum for polyethylene.
Figure 4B:
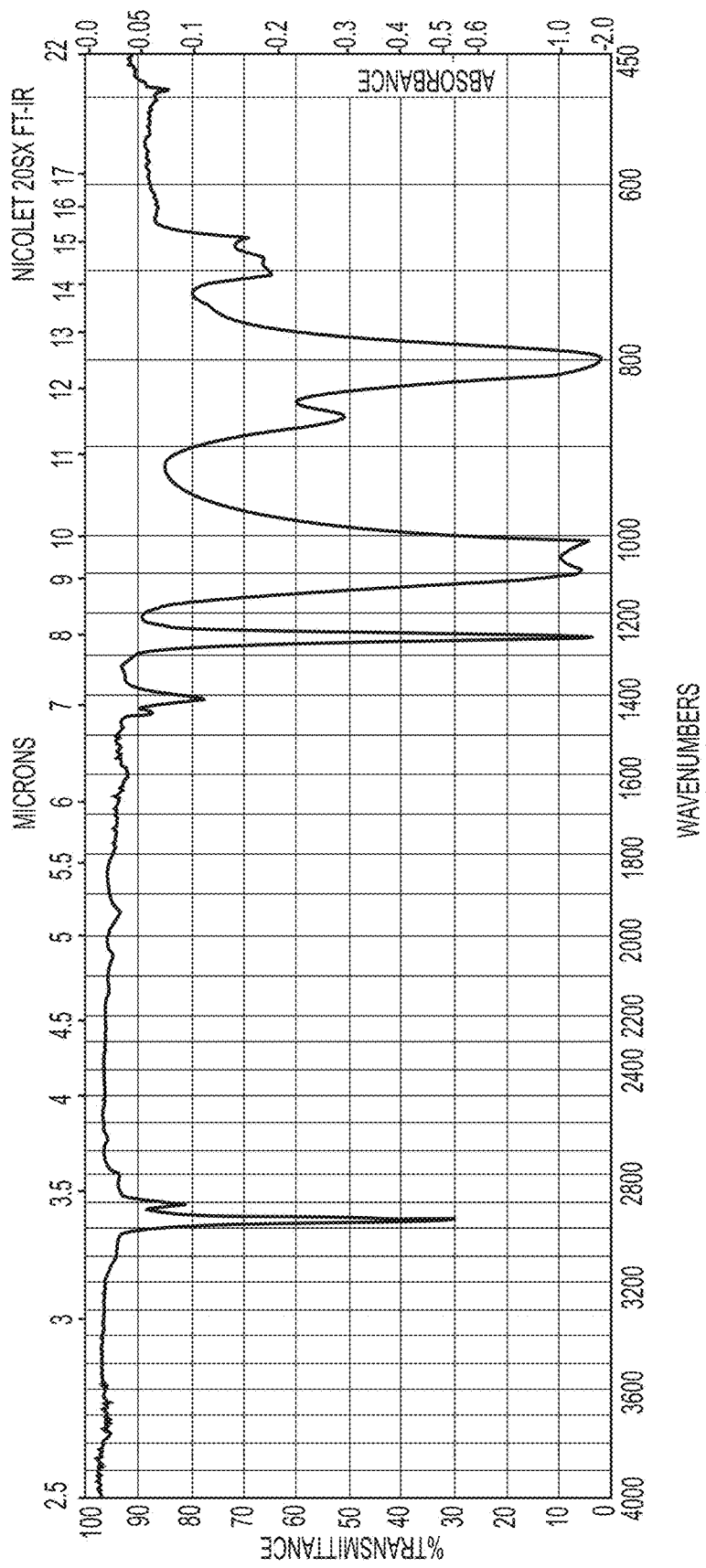
FIG. 4b illustrates an IR absorption spectrum for polydimethylsiloxane (PDMS)
Figure 4C:
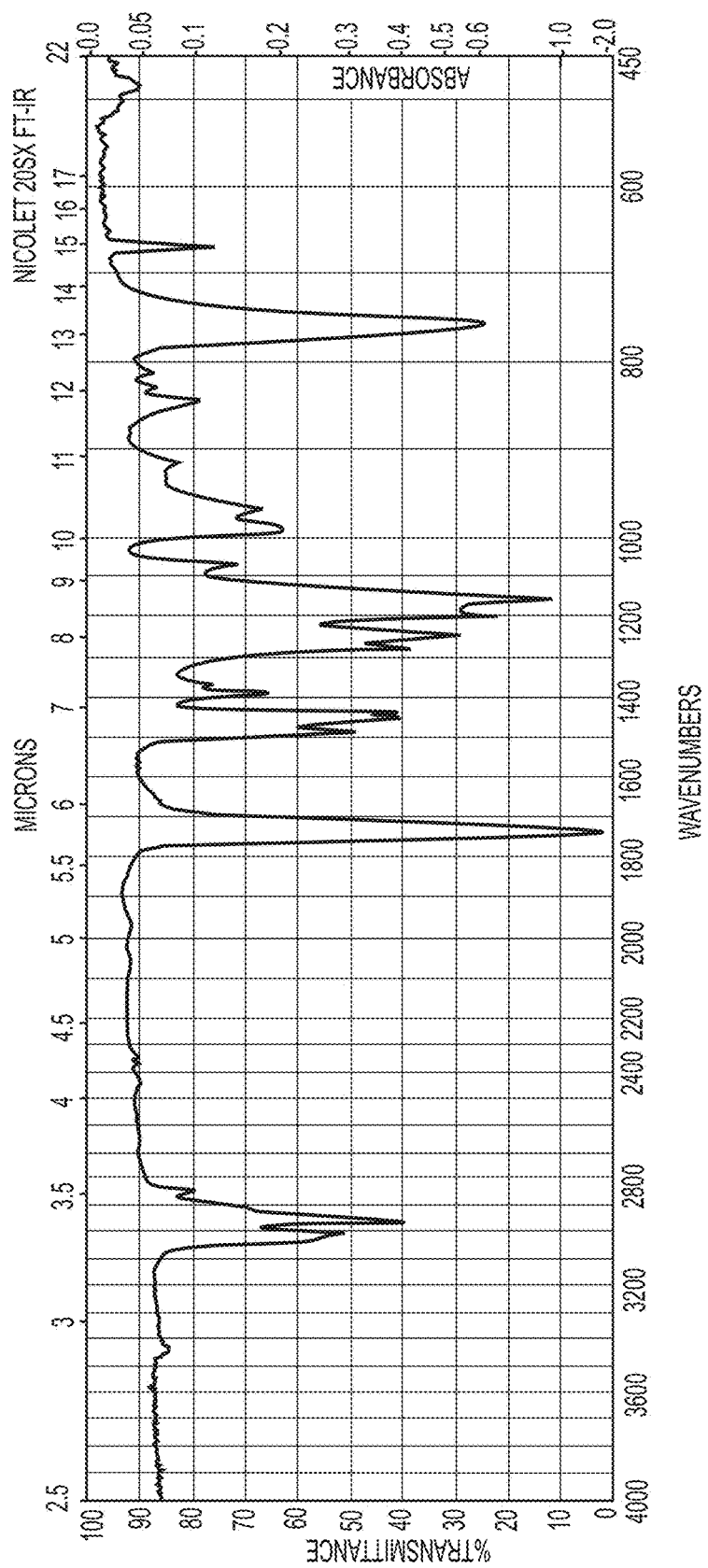
FIG. 4c illustrates an IR absorption spectrum for polymethylmethacrylate (PMMA)

The substrate for the chip can be a polymer or other material. The wavelength of heating is chosen to overlap a range including (a) absorbance of water according to FIG. 1, (b) emission wavelength of the chosen source, and (c) absorbance of the substrate material. For example, absorbance spectra of each material are shown in the figures. FIG. 3 illustrates COC and COP (provided under the names ZEONEX™, ZEONOR™, TOPAS™, APEL™, ARTON™). FIG. 4A illustrates polyethylene. FIG. 4B illustrates polydimethylsiloxane (PDMS). FIG. 4C illustrates polymethylmethacrylate (PMMA).

Figure 5:
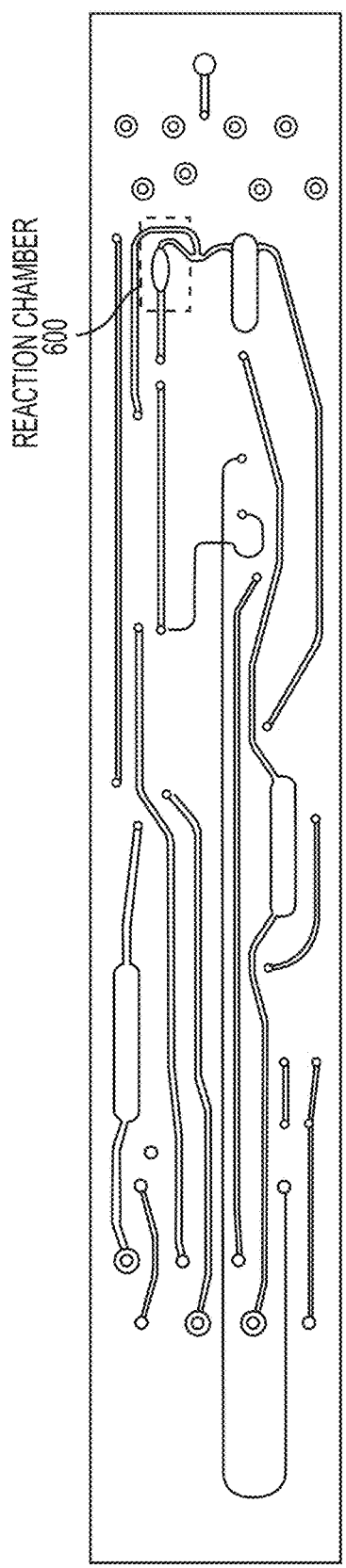
FIG. 5 schematically illustrates an exemplary integrated microfluidic chip that includes channels including channels for extraction, reaction, storage, waste, reaction, and separation, and a reaction chamber.
Figure 6:
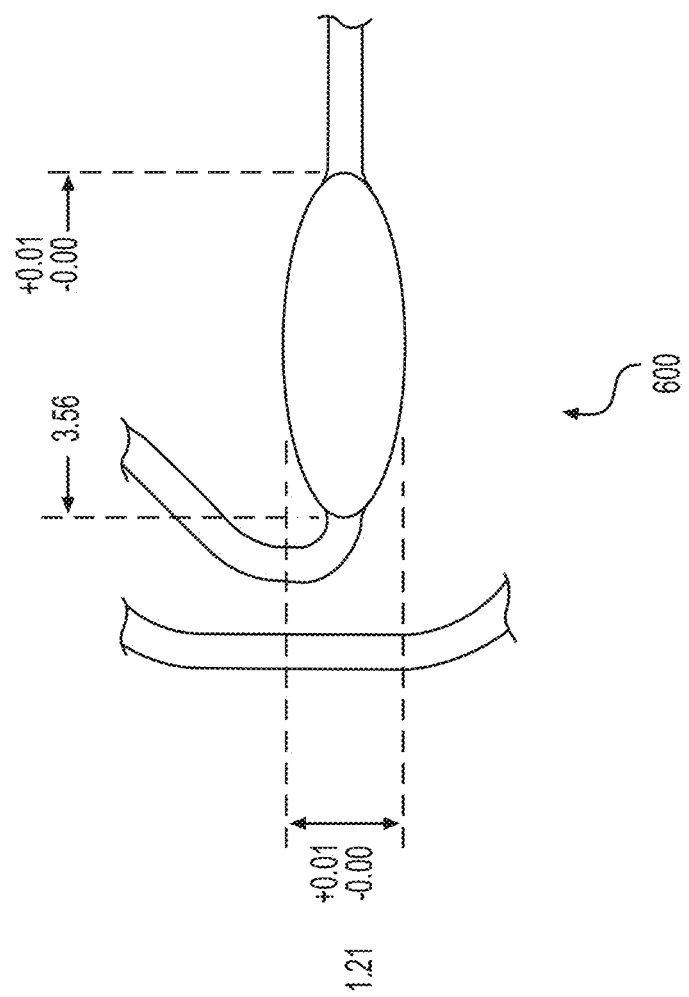
FIG. 6 schematically illustrates the reaction chamber of FIG. 5.

FIG. 5 schematically illustrates an exemplary integrated microfluidic chip with channels that includes channels for extraction, reaction, storage, waste, reaction, and separation. The reaction chamber is labeled reaction chamber 600. FIG. 6 illustrates an enlarged view of the reaction chamber 600 with exemplary measurements. FIGS. 5 and 6 are drawn to scale. The reaction chamber 600 is about 1.35 microliters in volume with a length of 3.56 mm and a width of 1.21 mm, and has an ellipsoid shape.

Figure 7B:
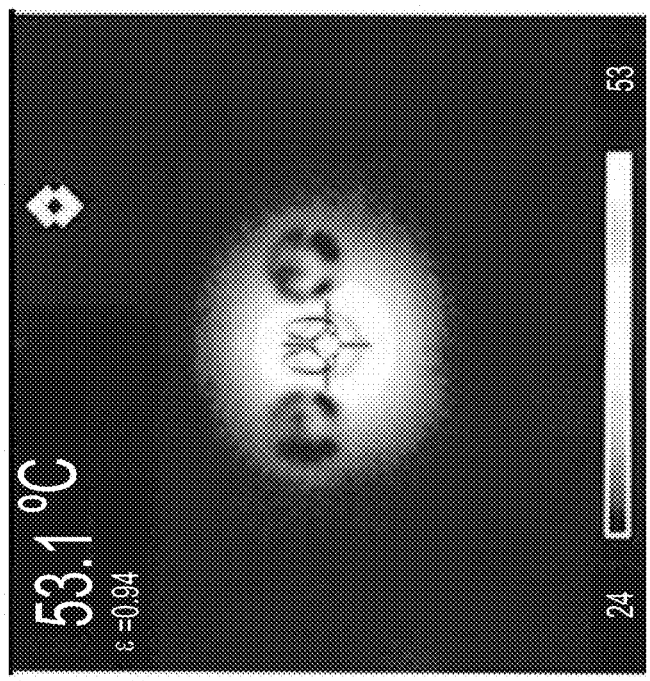
Figure 7A:
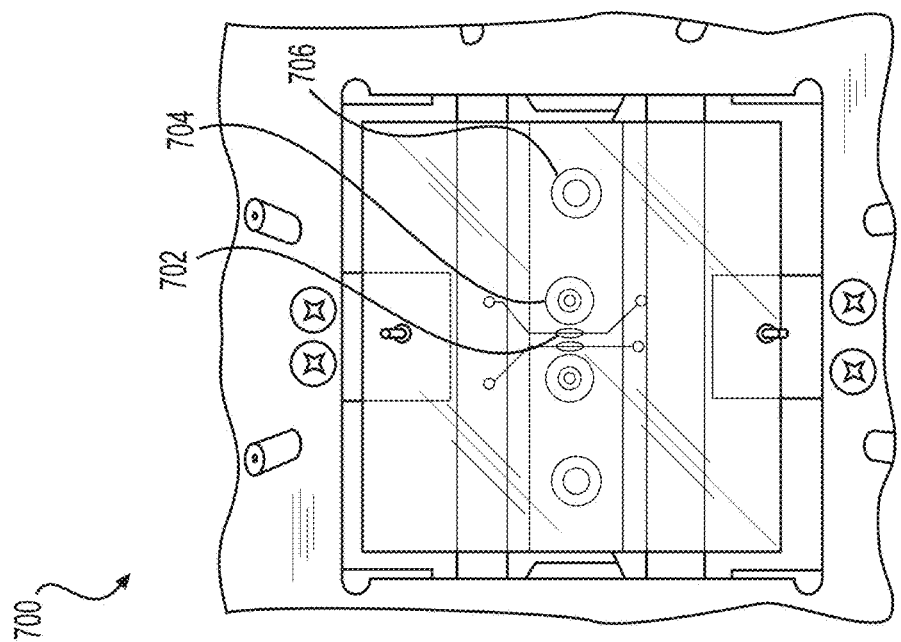
FIG. 7a illustrates a polymeric polymerase chain reaction microdevice over an IR laser source.

FIG. 7A is a top view of a polymeric PCR microdevice 700 over an IR laser to perform IR-mediated PCR in a polymeric microfluidic device. As illustrated in FIG. 7A, the microdevice 700 includes one or more reaction chambers 702, one or more IR laser (or laser outputs) 704, and one or more non-contact temperature sensors 706. The IR laser is used for heating, and is controlled via a non-contact temperature sensing method via a computer. As illustrated in the heat map of FIG. 7B, the IR laser source heats a small area encompassing the reaction chamber of the PCR. FIG. 7B is a heat map taken with an IR camera.

A temperature cycling profile obtained using a conventional thermal cycler was compared to a temperature cycling profile obtained after amplification using the IR laser system of FIG. 7A. Use of the IR laser system of FIG. 7A for microfluidic PCR amplification and a small reaction volume (~1 μL) allows for a decrease in total amplification time by as much as 6-fold.

FIGS. 8A-F illustrate a comparison of heat simulations using two different wavelengths directed to a cartridge/chamber combination. FIGS. 8A-C illustrate thermal effects on a chamber area using radiation of 1720 nm wavelength, and FIGS. 8D-F illustrate thermal effects using radiation of 1930 nm wavelengths. The temperature range in the simulation is room temperature (23° C.) to 95° C., which is the peak temperature of a thermocycling process in the PCR techniques used in this implementation. Other temperatures can be utilized in other techniques, and the teachings of this disclosure are not limited to the temperatures discussed herein.

The simulation is over 10 seconds: FIGS. 8*a* and 8*d* are at time=0 for the 1720 nm and 1930 nm laser, respectively. The substrate in ZEONEX® COC. FIGS. 8*b* and 8*e* are at time=5 seconds, and FIGS. 8*c* and 8*f* are at time=10 seconds. These figures show the difference in heat distribution over a broad area containing both the liquid sample and the chamber material (1720 nm) vs. a narrow heat distribution localized in the liquid sample (1930 nm). With a broader distribution of the heat, the chamber is at lower risk of a thermal gradient in the liquid sample, which would drive an inefficient and possibly incomplete reaction.

A microfluidic chip in accordance with this disclosure can be fully integrated to perform extraction with PCR on the same chip, extraction, PCR, and separation on the same chip, or extraction, PCR, separation, and detection with all the sample material being contained on the chip.

Non-contact heating can be combined with non-contact temperature sensing.

Laser light from a laser source can be transmitted through a fiber optic channel. Separate sources can be used for each channel, or a single source can be split into several channel sources.

Laser output can utilize corrective lensing to make it uniform across all channels. Here, a fiber optic laser is adapted with a lens that reduces a numerical aperture from 0.22 to a full angle from tip of optics of 16.77 degrees, which correlates to a spot size diameter of ~6.7 mm at the chip.

The implementations described herein can be with or without active cooling.

The laser source/output may have one or more of these specific requirements and design features in some implementations: 4 individually addressable and controllable channels; an output optical power at a wavelength of 1720 nm+/−10 nm center wavelength, with a spectral width of no more than 10 nm; a minimum power output for each channel of 1.0 Watt, for a total optical output power of a minimum of 4 Watts; and light from a fiber exits with a numerical aperture of 0.20+/−0.02, where a profile of the power intensity from the fiber is a maximum in the middle, and where the profile may be flat about the middle and then consistently decreases to the edge.

The chamber may have a variety of volumes from 100-10,000 nanoliters.

A channel leading to the chamber can be a variety of architectures.

Heating rates can be provided in a broad range.

The use of fiber optic cables, instead of complete hardware, can save space. Accordingly, the hardware for generating the light can be remote from an output of the light. The heat sensor (e.g., the pyrometer) can therefore be included on a same side of the chamber as the laser. This makes a complete detection device more compact, and facilitates miniaturization.

The chip can have a multitude of channels and a multitude of independent reaction chambers. There can be 1-20 different, but repeated channels for independent reactions on each chip. There can be multiple channels for each independent reaction.

Sample mixtures can include one or more nucleic acid molecules selected from the group consisting of double-stranded (ds) DNA, single-stranded (ss) DNA, and RNA.

A system can be constructed with the following specifications.

An IR light source module for use in heating micro samples of fluid and the surrounding containing material can be used in polymerase chain-reaction (PCR) process. The IR module is supplied with electrical power and control signals. The IR module can be provided with four separately addressable/controllable channels that will output from a fiber optic cable for each channel.

The IR light source module is a combination of control electronics, light source, thermal management, optics, and fiber optic delivery. This module is a self-contained unit forming a complete field replaceable unit (FRU). The IR light source module converts electrical power to optical power. Each channel is digitally controllable, and can be selectively enabled/disabled to activate or deactivate the respective channel. Each channel can be provided with an analog or digital input to control an output power of the respective channel.

The IR light source module can have the following external functional interfaces: input power, digital enable for each channel, analog or digital interface control of the optical power from each channel for each channel, and optical power output from fiber optic cables for each channel.

The IR light from the fiber exits with a Numerical aperture of 0.20+/−0.02. The profile of the power intensity from the fiber is a maximum in the middle. The profile may be flat about the middle and then consistently decreases to the edge.

An input voltage for the module can be 5 VDC (+/−0.5V), 12 VDC (+/−1.0V) or 24 VDC (+/−2V). The input voltages may be one or more of these values. Input voltage(s) can be selected to obtain the best unit efficiency and minimize power dissipated in heat.

Analog lines for controlling optical power are provided on a signal connector, where an input voltage range is 0 to 5 volts with 0 volts producing no output and 5 volts full output with a linear response between. The analog lines can have an input impedance greater than 10 kΩ, and can be connected to a voltage controller of a computer. A bandwidth of a signal and associated module response is greater than 0 KHz (DC) and less than 1 KHz. The rise time (Tr) of the laser output (10% to 90%) is related to the bandwidth (BW) by the relationship Tr=0.35/BW. For the 1 KHz bandwidth, the associated rise time is 350 microseconds.

The IR light from the module couples into fiber optic cables with a nominal diameter of 200 um and a numerical aperture (NA) of 0.22. The fiber optic cables are detachable from the module with an external bulkhead connector on the outside of the module. The laser module connector accepts a SMA905 connector. The output power of the model is measured at the output of the cable.

The emission of the laser is placed about 21 mm from the reaction chamber, the fiber optic laser is adapted with a lens that reduces the Numerical Aperture from 0.22 to a full angle from tip of optics of 16.77 degrees which correlates to a spot size diameter of ~6.7 mm at the chip.

Light output at 1720 nm (an infrared laser beam path) can consist of: (i) exiting the laser housing where it is immediately coupled into a (ii) optical fiber which connects to a (iii) lens assembly (with numerical aperture of 0.22), which expands the laser beam. The lens assemblies are mounted vertically so that exiting laser is directed upwards towards a cover plate of a module holding the chip. The chip can be mounted horizontally, relatively, such that a laser path is normal to a surface of the chip and/or a reaction chamber. The laser path can also be provided at an angle with respect to the normal. A temperature detecting path can be provided at an angle with respect to the normal, and can be provided so as not to interfere with the laser path.

Exemplary Laser Operating Procedures/Algorithmic Controls

Laser start-up procedure: The laser is powered when the system is turned on. Laser emission only occurs when command signals are sent via a software interface via the computer.

PCR procedure: Prior to operating the software interface, the chip should be in position in a holder with a cover in place. Only then should the software, which sends control signals to the laser, be used. Temperature sensing (e.g., pyrometer) feedback signals can indicate that the laser is in operation via the software interface, and the cover should not be removed while the PCR procedure is in operation.

Laser shut-down procedure: To ensure that the laser is off prior to removing the cover, a manual operational mode in the software can be selected and a zero output voltage can be input therein. By executing an appropriate command via the software, laser output can be turned off. This procedure can be repeated for each laser, and the temperature measurements can be observed to ensure the laser is not outputting any radiation. Also, disconnecting the power supply will turn off power to the laser.

Exemplary DNA Preparation

A buccal swab was obtained from a donor and added to 98 microliters of ZYGEM™ buffer and 2 microliters of PREPGEM™ enzyme. The resulting sample was incubated at 75° C. for 2 minutes and 95° C. for 2 minutes in a conventional thermal cycler.

POWERPLEX® 18: DNA was added to 2 microliters of POWERPLEX® mastermix, and 1 microliter of POWERPLEX® primers for a total volume of 10 microliters.

IDENTIFILER™: DNA was added to 5 microliters PYROSTART™ mastermix (FERMENTAS™), 2.25 microliters IDENTIFILER™ primers (from APPLIED BIOSYSTEMS), 0.25 microliters SPEEDSTAR™ DNA Polymerase (from TAKARA BIO), and 0.5 microliter of 10 mg/mL BSA for a total volume of 10 microliters.

Exemplary Thermal Cycling Procedures/Algorithmic Controls

PROMEGA POWERPLEX®: 96° C. for 1 minute, 30 cycles of (94° C. for 5 seconds, 60° C. for 10 seconds, 72° C. for 10 seconds), and finally 60° C. for 60 seconds. Temperatures are maintained by controlled heating and algorithmic processing by the computer, in conjunction with passive or active cooling.

INDENTIFILER™: 95° C. for 1 minute, 32 cycles of (95° C. for 5 seconds, 59° C. for 10 seconds, 72° C. for 10 seconds), and finally 60° C. for 60 seconds. Temperatures are maintained by controlled heating and algorithmic processing by the computer, in conjunction with passive or active cooling.

Exemplary Integrated Chip Thermal Cycling Procedure/Control Algorithm

Using LIFE TECHNOLOGIES IDENTIFILER™, samples were held at an initial temperature of 95° C. for 60 seconds, for an initial denaturing step. Then, there were 26 cycles of (a) being heated with the IR laser to 95° C. and held for 5 seconds, (b) the source was turned off and passively cooled to 60° C. at 2.1° C./s and held for 10 second, and (c) then heated to 72° C. at a rate of 3.7° C./s and held for 10 seconds. Then, there was a final extension for 5 minutes. The amplification results were then separated on the chip by electrophoresis.

Using PROMEGA POWERPLEX18D™, samples were held at an initial temperature of 95° C. for 60 seconds, for an initial denaturing step. Then, there were 27 cycles of: (a) being heated with the IR laser to 95° C. and held for 5 seconds, (b) the source was turned off and passively cooled to 60° C. at 2.1° C./s and held for 10 seconds, and (c) then heated to 72° C. at a rate of 3.7° C./s and held for 10 seconds. Then, there was a final extension for 5 minutes. The amplification results were then separated on the chip by electrophoresis.

In another implementation, using LIFE TECHNOLOGIES IDENTIFILER™, samples were held at an initial temperature of 94° C. for 60 seconds, for an initial denaturing step. Then, there were 27 cycles of (a) being heated with the IR laser to 94° C. and held for 5 seconds, (b) the source was turned off and passively cooled to 59° C. at 2.1° C./s and held for 20 second. Then, there was a final extension for 5 minutes at 72° C. The amplification results were then separated on the chip by electrophoresis.

Using PROMEGA POWERPLEX18D™, samples were held at an initial temperature of 94° C. for 60 seconds, for an initial denaturing step. Then, there were 27 cycles of: (a) being heated with the IR laser to 94° C. and held for 10 seconds, (b) the source was turned off and passively cooled to 59° C. at 2.1° C./s and held for 40 seconds Then, there was a final extension for 5 minutes at 60° C. The amplification results were then separated on the chip by electrophoresis.

However, other times and temperatures can be utilized in accordance with the teachings of this disclosure, and the above-mentioned values can be approximate values or average values that fall within a defined range of the approximate values for the corresponding period of time.

Figure 9:
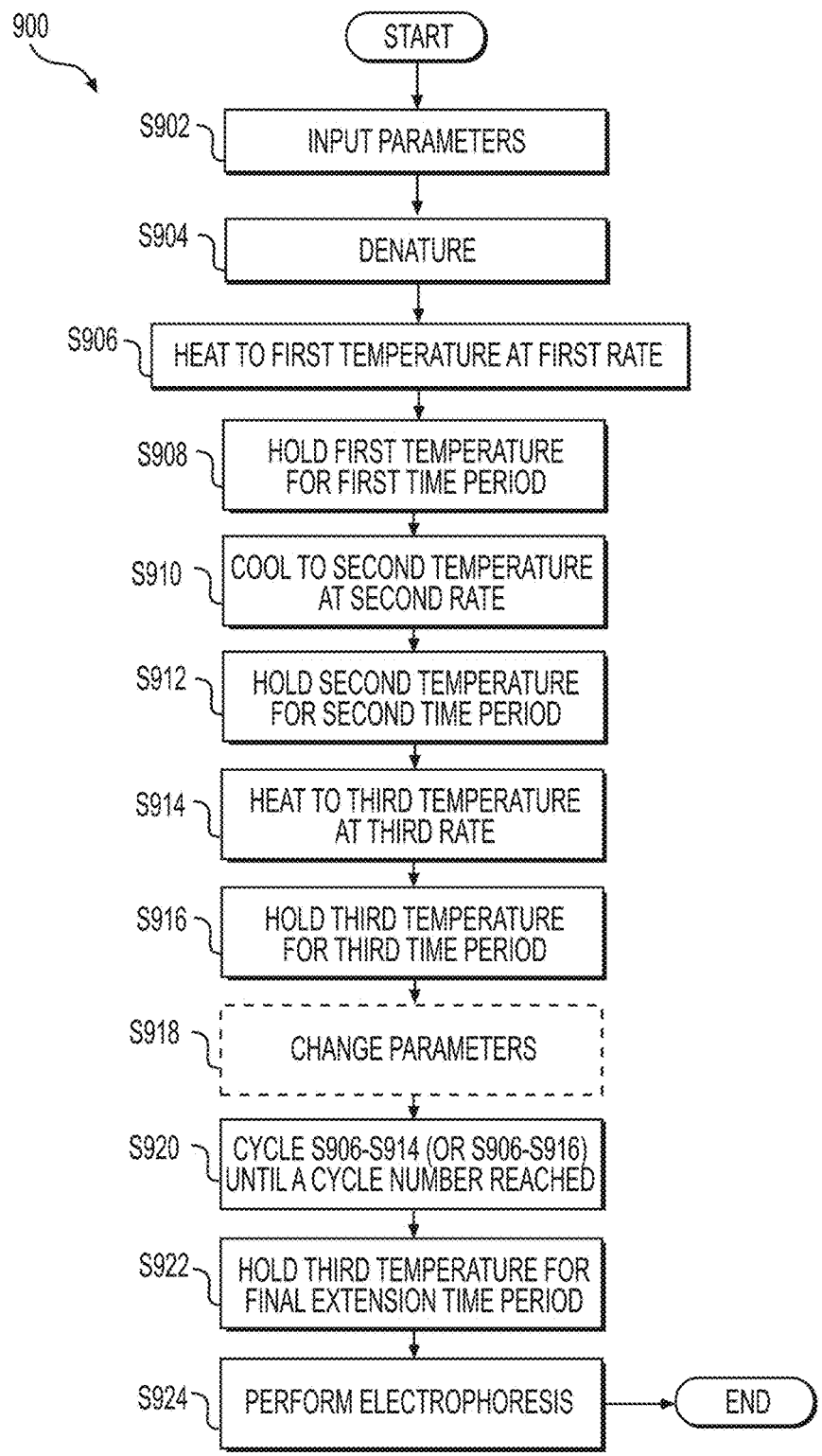
FIG. 9 is an algorithmic flowchart of an exemplary process.

FIG. 9 is a flowchart that illustrates an exemplary algorithmic process 900 in accordance with this disclosure. At S902, parameters are input into a system, processing system or computer to control the process. Exemplary parameters include materials of reaction chamber, type of heating source(s), type of cooling source(s), type of temperature sensing device(s), amount of fluid in a reaction chamber, primary component of the fluid in the reaction chamber, temperatures, hold times, number of cycles, and operating mode. The operating mode can be set to automatic, semi-automatic or manual, to offer a user varying levels of interaction throughout a complete process. The parameters can be input via a graphical user interface of a computer via a peripheral and a display. The list of parameters is not exhaustive. The parameters can be predefined in a data file of the computer, and accessed by merely selecting one or a few options. Tabled data files can also be used to select predefined procedure setups. The computer can also be set to default to an expected heat source, passive cooling, and an expected temperature sensing device. The default can further include pre-set temperatures, hold times, rates of temperature changes and number of cycles.

After the parameters have been input, selected and loaded into the computer, or otherwise defined in a processing system at S902, and the equipment (i.e., the microfluidic chip, holder, heat source, cooling source, and temperature sensor) and fluid are properly established, a denaturing step can be provided at S904. The denaturing step at S904 includes holding the fluid sample at an initial denaturing temperature for an initial time period.

After the denaturing step at S904, heating of the sample, the fluid and/or the reaction chamber (herein simply referred to as heating) commences at S906. At S906, heating is performed at a first heating rate, where an amount of heating is applied through the heat source to achieve a predefined first heating rate until a first temperature is achieved. In another implementation, the heating rate (i.e., the first rate) may not be defined. The first temperature is held for a first time period at S908.

Cooling of the sample, the fluid and/or the reaction chamber (herein simply referred to as cooling) is performed at S910, either passively or actively, at or at least at a second rate (i.e., a second cooling rate) to a second temperature. In another implementation, the second cooling rate (i.e., the second rate) may not be defined. The second temperature is held for a second time period at S912.

At S914, heating is performed at a third heating rate, where an amount of heating is applied through the heat source to achieve a predefined third heating rate until a third temperature is achieved. In another implementation, the third heating rate (i.e., the third rate) may not be defined. The third temperature is held for a third time period at S916.

The steps of S906-S916 define a cycle. The parameters (i.e., heating/cooling variables) can be optionally adjusted at S918 after each cycle, based on a predefined input if an automatic mode is selected, or based on a user input if a semi-automatic mode is selected. In a manual mode, the user has control over each step/procedure, and the computer does not advance one or more aspects of the algorithm until user input has been received.

The steps S906-S916 or S906-S918 are cycled repeatedly at S920 until a number of cycles have been completed. This number can be predefined or selected by a user in real-time. Also, the number can be selected by the computer, automatically, based on a sensor input relating to an observable or detectable property of the sample.

After the cycling has completed, the third temperature is held for a final extension time period at S922, and electrophoresis is performed at S924.

In the above algorithm, the heating and cooling rates can be monitored by periodically processing temperature readings, and can be controlled by adjusting an amount of heating by a heat source and an amount of cooling provided by an active cooling device. When it is known that certain heating/cooling rates are achieved due to a particular heating/cooling arrangement, it may not be necessary to monitor heating/cooling rates. Further, the heating/cooling rates may merely be monitored to ensure certain thresholds are exceeded.

In accordance with the previously discussed exemplary implementation, the following settings can be applied:
  Sample/Fluid Volume: 10 ml
  Denaturing: 95° C. for 60 seconds;
  Cycles: 27
  First temperature: 95° C.;
  First holding time: 5 seconds;
  First rate: >3° C./s (positive, heating);
  Second temperature: 60° C.;
  Second holding time: 10 seconds;
  Second rate: 2.1° C./s (negative, cooling);
  Third temperature: 72° C.;
  Third holding time: 10 seconds;
  Third rate: 3.7° C./s (positive, heating); and
  Final extension time period: 5 minutes.

In accordance with another exemplary implementation, the following settings can be applied:
  Sample/Fluid Volume: <10 ml
  Denaturing: 50-96° C. for 60 seconds;
  Cycles: 20-35
  First temperature: 50-96° C.;
  First holding time: 2-10 seconds;
  First rate: >3° C./s (positive, heating);
  Second temperature: 50-96° C.;
  Second holding time: 5-20 seconds;
  Second rate: >2° C./s (negative, cooling);
  Third temperature: 50-96° C.;
  Third holding time: 5-20 seconds;
  Third rate: >3° C./s (positive, heating); and
  Final extension time period: 2-15 minutes.

Blocks of computer architecture shown or described herein can be implemented in a single processing system, or distributed across a plurality of processing systems, which may be referred to as processors. For instance, each of the blocks of architecture can be a discrete processor, system or logic component.

Figure 10:
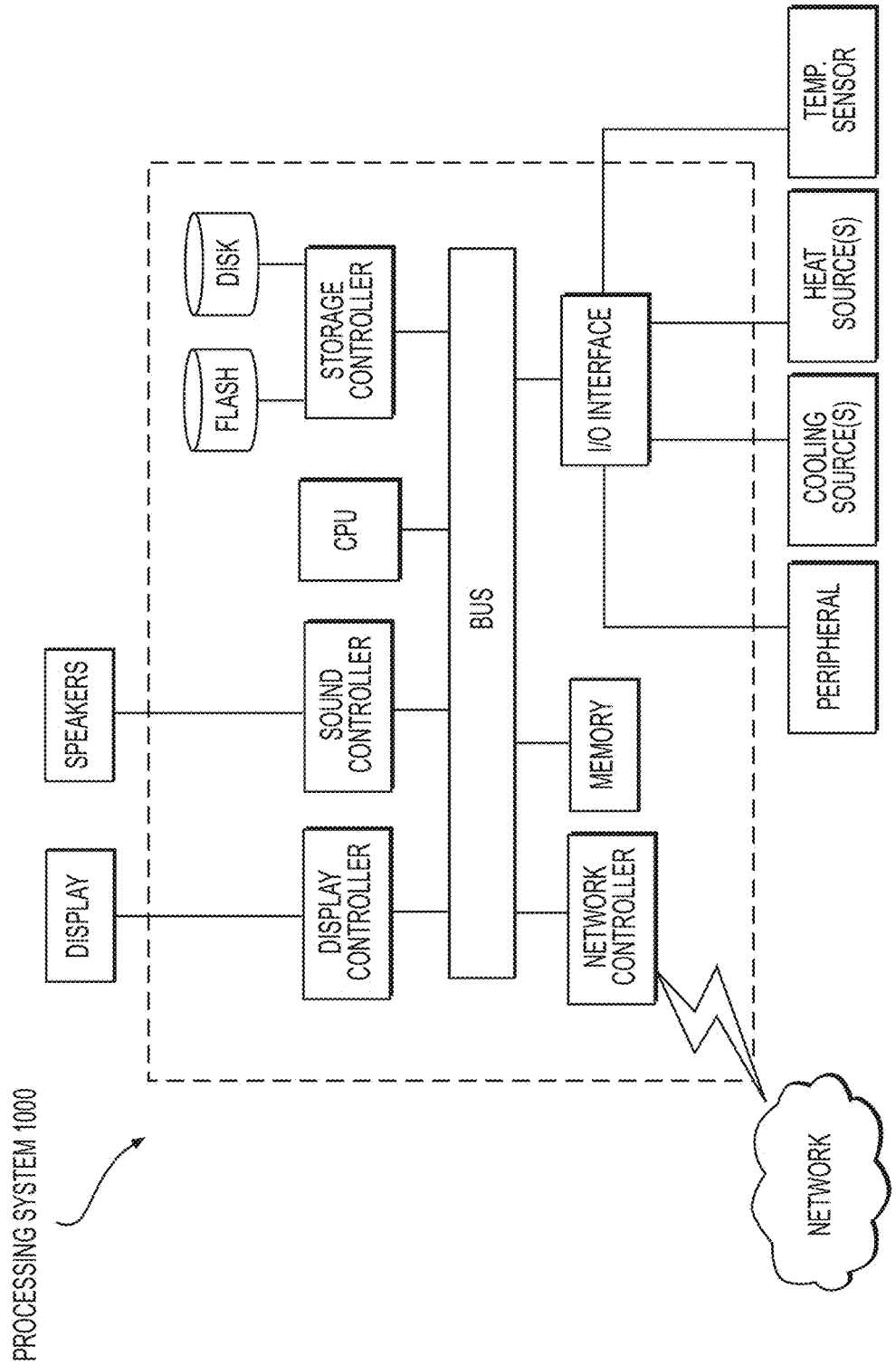
FIG. 10 schematically illustrates an exemplary processing system or computer.

FIG. 10 illustrates an exemplary processing system or processor 1000. One or more of such processing systems can be utilized in or to execute one or more algorithms, or portions thereof, or one or more architecture blocks, or portions thereof, in accordance with the descriptions provided herein.

The exemplary processing system 1000 can be implemented using one or more microprocessors or the equivalent, such as a central processing unit (CPU) and/or at least one application specific processor ASP (not shown). The microprocessor is a circuit that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure. Other storage mediums can be controlled via a controller, such as a disk controller, which can control a hard disk drive or optical disk drive.

The microprocessor or aspects thereof, in alternate implementations, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU. Control circuitry provided by one or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output)

interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The I/O interface is also connected to the cooling source(s), the heat source(s) and the temperature sensor.

The above-noted components can be coupled to a network, such as the Internet or a local intranet, via a network interface for the transmission or reception of data, including controllable parameters. A central BUS is provided to connect the above hardware components together and provides at least one path for digital communication there between.

Suitable software, such as an operating system or an application, can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The procedures and routines described herein can be embodied as a system, method or computer program product, and can be executed via one or more dedicated circuits or programmed processors. Accordingly, the descriptions provided herein may take the form of exclusively hardware, exclusively software executed on hardware (including firmware, resident software, micro-code, etc.), or through a combination of dedicated hardware components and general processors that are configured by specific algorithms and process codes. Hardware components are referred to as a "circuit," "module," "unit," "device," or "system." Executable code that is executed by hardware is embodied on a tangible memory device, such as a computer program product. Examples include CDs, DVDs, flash drives, hard disk units, ROMs, RAMs and other memory devices.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

The invention claimed is:

1. An apparatus, comprising:
a plurality of reaction chambers, each reaction chamber to hold a fluid;
a heat source to heat the reaction chamber and the fluid, wherein the heat source does not contact the reaction chamber or the fluid, and the reaction chamber and the fluid separately absorb heat radiation from the heat source, the heat source including a plurality of infrared lasers, each infrared laser having a different wavelength, outputs of the infrared lasers being coupled together as to form a single heat source for the reaction chamber;
a temperature sensor to acquire a temperature of the reaction chamber and/or the fluid; and
control circuitry configured to control the heat source independently for each of the reaction chambers according to a corresponding cycling profile for a chemical or biochemical reaction in the fluid to cycle the heat source between heating and not heating each of the reaction chambers and the fluid based on a corresponding temperature acquired by the temperature sensor.

2. The apparatus according to claim 1, wherein:
the heat source includes an output for non-contact heating for each of the reaction chambers, and
the temperature sensor is to acquire a separate temperature for each of the reaction chambers.

3. The apparatus according to claim 2, further comprising:
a microfluidic chip that includes the plurality of reaction chambers and cyclic olefin copolymer (COC).

4. The apparatus according to claim 1, wherein at least one of the infrared lasers operates at 1720 nm+/−10 nm center wavelength.

5. The apparatus according to claim 1, wherein the temperature sensor is a non-contact sensor that does not contact the reaction chamber or the fluid.

6. The apparatus according to claim 5, wherein the temperature sensor includes one or more pyrometers or one or more infrared cameras.

7. The apparatus according to claim 1, wherein the cycling profile includes following steps:
   (a) heating to a first temperature at a first rate;
   (b) holding the first temperature for a first holding time;
   (c) cooling to a second temperature at a second rate;
   (d) holding the second temperature for a second holding time;
   (e) heating to a third temperature at a third rate; and
   (f) holding the third temperature for a third holding time.

8. The apparatus according to claim 7, wherein, in the cycling profile, the steps (a)-(f) are repeated for a predetermined number of cycles.

9. The apparatus according to claim 8, wherein, for a last one of the cycles, the third temperature is held for a final extension time period that is longer than the third holding time.

10. The apparatus according to claim 9, wherein the cycling profile includes, prior to the step (a) in a first one of the cycles, a denaturing step of holding a denaturing temperature for a denaturing time period.

11. The apparatus according to claim 10, wherein the control circuitry is configured to control the heat source according to the cycling profile such that following conditions are satisfied:
   volume of the fluid ≤10 ml;
   the predetermined number of cycles=20-35;
   the first temperature=50-96° C.;
   the first holding time=2-20 seconds;
   the first rate=>2° C./s;
   the second temperature=50-96° C.;
   the second holding time=5-60 seconds;
   the second rate: <−1° C./s;
   the third temperature=50-96° C.;
   the third holding time=5-60 seconds;
   the third rate=>2° C./s; and
   the final extension time period=1-15 minutes.

12. The apparatus according to claim 11, wherein the control circuitry is configured to control the heat source according to the cycling profile such that the following conditions are satisfied:
   denaturing temperature=50-96°; and
   denaturing time period is equal to or more than 60 seconds.

13. The apparatus according to claim 10, wherein the control circuitry is configured to control the heat source according to the cycling profile such that following conditions are satisfied:
   volume of the fluid ≤10 ml;
   the predetermined number of cycles is approximately 27;
   the first temperature is approximately 95° C.,
   the first holding time is approximately 5 seconds;
   the first rate is approximately >3° C./s;
   the second temperature is approximately 60° C.;
   the second holding time is approximately 10 seconds;
   the second rate is approximately −2.1° C./s;
   the third temperature is approximately 72° C.;
   the third holding time is approximately 10 seconds; and
   the third rate is approximately 3.7° C./s.

14. The apparatus according to claim 10, wherein the control circuitry is configured to control the heat source according to the cycling profile such that following conditions are satisfied:
   the first temperature is higher than the second and third temperatures;
   the third temperature is higher than the second temperature; and
   the first holding time is less than the second and third holding times.

15. The apparatus according to claim 1, further comprising:
   an active or passive cooler to cool the reaction chamber and/or the fluid, wherein
   when the active cooler is provided, the control circuit is configured to control the active cooler to provide cooling in accordance with the cycling profile.

16. The apparatus according to claim 1, wherein:
   the heat source includes a fiber optic channel to output infrared light to the reaction chamber and the fluid to heat the reaction chamber and the fluid, and
   the fiber optical channels include corrective lenses at output ends thereof.

17. A method for a reaction, comprising:
   independently controlling, by control circuitry, heating and cooling of each of a plurality of reaction chambers, each contains a fluid in which an reaction is to occur, in accordance with a corresponding cycling profile based on sensing a corresponding temperature of each of the reaction chambers or the fluid, each cycling profile including:
   (a) heating to a first temperature at a first rate;
   (b) holding the first temperature for a first holding time;
   (c) cooling to a second temperature at a second rate;
   (d) holding the second temperature for a second holding time;
   (e) heating to a third temperature at a third rate; and
   (f) holding the third temperature for a third holding time,
   wherein a reaction chamber is heated by a heat source including a plurality of infrared lasers, each infrared laser having a different wavelength, outputs of the infrared lasers being coupled together as to form a single heat source for the reaction chamber.

18. A non-transitory computer-readable medium including computer-executable instructions, which when executed by control circuitry, cause the control circuitry to perform the method according to claim 17.

19. An apparatus, comprising:
   a reaction chamber to hold a fluid;
   a non-contact heat source to heat the reaction chamber and the fluid, wherein the heat source does not contact the reaction chamber or the fluid, and the reaction chamber and the fluid separately absorb heat radiation from the heat source;
   a temperature sensor to acquire a temperature of the reaction chamber and/or the fluid; and
   control circuitry configured to control the heat source according to a cycling profile for a chemical or biochemical reaction in the fluid to cycle the heat source between heating and not heating the reaction chamber and the fluid based on the temperature acquired by the temperature sensor, wherein the heat source includes an output for non-contact heating for each of the reaction chambers, the temperature sensor is to acquire a separate temperature for each of the reaction chambers, and the control circuitry is configured to control the heat source independently for each of the reaction chambers based on the respective temperatures acquired by the temperature sensor and the cycling profile, wherein the heat source includes one or more infrared lasers and the one or more infrared lasers operate at 1720 nm+/−10 nm center wavelength.

* * * * *